(12) United States Patent
Yamamoto et al.

(10) Patent No.: US 9,522,857 B2
(45) Date of Patent: Dec. 20, 2016

(54) 3,3',4,4'-TETRAALKYL CYCLOHEXYLBENZENE AND METHOD FOR PRODUCING SAME

(75) Inventors: Yasushi Yamamoto, Ube (JP); Hikaru Yatabe, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 280 days.

(21) Appl. No.: 14/118,190

(22) PCT Filed: May 18, 2012

(86) PCT No.: PCT/JP2012/062792
§ 371 (c)(1),
(2), (4) Date: Nov. 15, 2013

(87) PCT Pub. No.: WO2012/157749
PCT Pub. Date: Nov. 22, 2012

(65) Prior Publication Data
US 2014/0058143 A1    Feb. 27, 2014

(30) Foreign Application Priority Data

May 18, 2011 (JP) .................................. 2011-111111

(51) Int. Cl.
| | | |
|---|---|---|
| *C07C 13/38* | (2006.01) | |
| *C07C 15/14* | (2006.01) | |
| *C07C 2/76* | (2006.01) | |
| *B01J 23/44* | (2006.01) | |
| *B01J 23/46* | (2006.01) | |
| *B01J 29/08* | (2006.01) | |
| *C07C 13/28* | (2006.01) | |
| *C07D 407/04* | (2006.01) | |
| *C07C 2/74* | (2006.01) | |
| *C07C 5/367* | (2006.01) | |

(52) U.S. Cl.
CPC ............... *C07C 2/76* (2013.01); *B01J 23/44* (2013.01); *B01J 23/462* (2013.01); *B01J 29/088* (2013.01); *C07C 2/74* (2013.01); *C07C 5/367* (2013.01); *C07C 13/28* (2013.01); *C07D 407/04* (2013.01); *C07C 2101/14* (2013.01); *C07C 2521/04* (2013.01); *C07C 2521/08* (2013.01); *C07C 2521/12* (2013.01); *C07C 2521/16* (2013.01); *C07C 2521/18* (2013.01); *C07C 2523/44* (2013.01); *C07C 2523/63* (2013.01); *C07C 2529/08* (2013.01); *C07C 2529/18* (2013.01); *C07C 2529/40* (2013.01); *C07C 2529/50* (2013.01); *C07C 2529/70* (2013.01); *Y02P 20/52* (2015.11)

(58) Field of Classification Search
CPC .................................. C07C 13/38; C07C 15/14
USPC ........................................... 585/23, 25, 425
See application file for complete search history.

(56) References Cited

U.S. PATENT DOCUMENTS

| | | | | | |
|---|---|---|---|---|---|
| 4,219,687 | A | * | 8/1980 | Dolhyj ...................... | C07C 2/74 208/144 |
| 5,053,571 | A | * | 10/1991 | Makkee .................... | C07C 2/74 585/425 |
| 5,243,067 | A | * | 9/1993 | Shiotani .................. | C07C 51/09 560/76 |
| 6,914,152 | B2 | | 7/2005 | Yamamoto et al. | |
| 8,178,728 | B2 | * | 5/2012 | Cheng .................. | B01J 29/7088 568/361 |
| 8,853,482 | B2 | * | 10/2014 | Wang ........................ | C07C 4/18 585/320 |
| 8,921,604 | B2 | * | 12/2014 | Becker ...................... | C07C 2/66 568/342 |
| 2009/0299111 | A1 | * | 12/2009 | Kanbara .................. | C07C 2/862 585/23 |
| 2013/0197261 | A1 | * | 8/2013 | Yamamoto ............ | C07C 67/313 560/77 |
| 2014/0275606 | A1 | * | 9/2014 | Bai .......................... | C07C 2/74 560/77 |

(Continued)

FOREIGN PATENT DOCUMENTS

| | | |
|---|---|---|
| JP | A-S48-40753 | 6/1973 |
| JP | A-S48-54048 | 7/1973 |

(Continued)

OTHER PUBLICATIONS

Office Action in Chinese Patent Application No. 201280030843.5, dated Sep. 26, 2014.

(Continued)

*Primary Examiner* — Ellen McAvoy
(74) *Attorney, Agent, or Firm* — Knobbe Martens Olson & Bear LLP

(57) ABSTRACT

A 3,3',4,4'-tetraalkyl cyclohexylbenzene represented by the general formula (1):

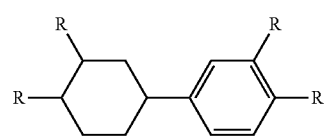

(1)

in which R represents an alkyl group having 1 to 4 carbon atoms, which may be easily converted into a 3,3',4,4'-biphenyltetracarboxylic acid and a 3,3',4,4'-biphenyltetracarboxylic dianhydride thereof, which are starting materials for a polyimide, via a 3,3',4,4'-tetraalkylbiphenyl; and a method for producing the same.

1 Claim, No Drawings

(56) References Cited

U.S. PATENT DOCUMENTS

| | | | |
|---|---|---|---|
| 2014/0275607 A1* | 9/2014 | Dakka | C07C 2/74 560/77 |
| 2014/0371498 A1* | 12/2014 | Kuechler | C07C 2/74 585/252 |

FOREIGN PATENT DOCUMENTS

| | | |
|---|---|---|
| JP | A-S48-96566 | 12/1973 |
| JP | A-S61-22045 | 1/1986 |
| JP | B-H05-3857 | 1/1993 |
| JP | A-2003-064021 | 3/2003 |
| JP | A-2005-342644 | 12/2005 |
| JP | B-H05-3857 | 12/2005 |
| JP | B-3959602 | 8/2007 |
| WO | WO 2007/013469 A1 | 2/2007 |

OTHER PUBLICATIONS

International Preliminary Report on Patentability in corresponding PCT/JP2012/062792 dated Nov. 19, 2013.

* cited by examiner

3,3',4,4'-TETRAALKYL CYCLOHEXYLBENZENE AND METHOD FOR PRODUCING SAME

This application is the U.S. National Phase under 35 U.S.C. §371 of International Application No. PCT/JP2012/062792, filed May 18, 2012, designating the U.S., and published in Japanese as WO 2012/157749 on Nov. 22, 2012, which claims priority to Japanese Patent Application No. 2011-111111 filed May 18, 2011, the entire content of which is incorporated herein by reference.

TECHNICAL FIELD

The present invention relates to a novel 3,3',4,4'-tetraalkyl cyclohexylbenzene (hereinafter, sometimes referred to as s-TACHB). The compound is a useful compound which may be easily converted into, for example, a 3,3',4,4'-biphenyltetracarboxylic acid (hereinafter, sometimes referred to as s-BPTA) and a 3,3',4,4'-biphenyltetracarboxylic dianhydride thereof (hereinafter, sometimes referred to as s-BPDA), which are a starting material for a polyimide, via a 3,3',4,4'-tetraalkylbiphenyl.

BACKGROUND ART

Conventionally, a 3,3',4,4'-biphenyltetracarboxylic acid and a 3,3',4,4'-biphenyltetracarboxylic dianhydride thereof, which may be produced by dehalogenative coupling of a halogenated phthalic acid (see, for example, Patent Literature 1) or oxidation of methyl group of a 3,3',4,4'-tetramethylbiphenyl (s-TMBP) (see, for example, Patent Literature 2), are widely known as a starting material for a polyimide.

As a method for producing the 3,3',4,4'-tetramethylbiphenyl (s-TMBP), a method comprising a step of dimerizing o-xylene using a Grignard reagent in the presence of copper chloride to produce s-TMBP, for example, is disclosed (see, for example, Patent Literature 3). Furthermore, a method comprising a step of dimerizing o-xylene in the presence of palladium bis(trifluoroacetate), copper acetate, and pyridine-2-carboxylic acid to produce TMBP (a mixture of s-TMBP and a-TMBP (2,3,3',4'-tetramethylbiphenyl)), particularly with a-TMBP selectivity of 70 mol % or more (production ratio of s-TMBP (s/a)=30/70 or less) is disclosed (see, for example, Patent Literature 4).

Meanwhile, as a method for producing a compound having a cyclohexylbenzene skeleton, a method comprising a step of reacting benzene with hydrogen in the presence of a catalyst for producing cyclohexylbenzene, which contains a hydrogenation catalyst comprising a mesoporous material as a support, and a solid acid catalyst modified with a metal of Group 2 or Group 3, to produce cyclohexylbenzene, for example, is disclosed (see, for example, Patent Literature 5).

CITATION LIST

Patent Literature

Patent Literature 1: Japanese Patent Publication No. H05-3857
Patent Literature 2: Japanese Patent Laid-Open Publication No. 548-54048
Patent Literature 3: Japanese Patent Laid-Open Publication No. 561-22045
Patent Literature 4: Japanese Patent Publication No. 3959602
Patent Literature 5: Japanese Patent Laid-Open Publication No. 2005-342644

SUMMARY OF INVENTION

Technical Problem

The method described in Patent Literature 3 has a problem in that a Grignard reagent must be used, and therefore the reaction is complicated. Meanwhile, the method described in Patent Literature 4 is directed to a method for selectively producing a-TMBP and the selectivity of s-TMBP is insufficient, although TMBP may be easily produced from o-xylene.

Patent Literature 5 discloses a method for producing cyclohexylbenzene. However, no consideration is given to a method for selectively obtaining only a desired product (for example, 3,3',4,4'-tetraalkyl cyclohexylbenzene) from among numerous by-products (regioisomers) when a compound having a cyclohexylbenzene skeleton and substituent(s) is produced from benzene having substituent(s) such as o-xylene as a starting material. Therefore, this method could not be easily applied.

Under such circumstances, there is need for a method capable of easily converting an o-dialkylbenzene (benzene having substituent(s)) such as o-xylene into 3,3',4,4'-tetraalkylbiphenyl such as s-TMBP, and a precursor or an intermediate therefor.

Accordingly, an object of the present invention is to provide a 3,3',4,4'-tetraalkyl cyclohexylbenzene which may be easily converted into a 3,3',4,4'-biphenyltetracarboxylic acid and a 3,3',4,4'-biphenyltetracarboxylic dianhydride thereof, which are a starting material for a polyimide, via a 3,3',4,4'-tetraalkylbiphenyl.

Another object of the present invention is to provide a method for producing a 3,3',4,4'-tetraalkyl cyclohexylbenzene with high yield and high selectivity only from an o-dialkylbenzene, which is a single starting compound, efficiently and easily.

Solution to Problem

The present invention relates to the following items.
1. A 3,3',4,4'-tetraalkyl cyclohexylbenzene represented by the general formula (1):

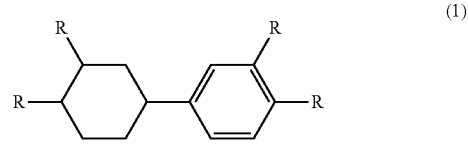

wherein R represents an alkyl group having 1 to 4 carbon atoms.

2. A method comprising
reacting an o-dialkylbenzene represented by the general formula (2):

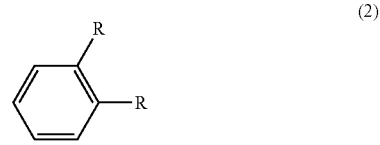

wherein R represents an alkyl group having 1 to 4 carbon atoms,
with hydrogen to perform a hydroalkylation of the o-dialkylbenzene, thereby producing a 3,3',4,4'-tetraalkyl cyclohexylbenzene represented by the general formula (1):

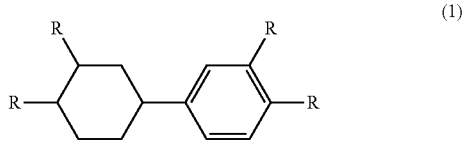

(1)

wherein R is defined as above.

3. The method for producing a 3,3',4,4'-tetraalkyl cyclohexylbenzene according to Item 2, wherein the hydroalkylation of the o-dialkylbenzene is performed by reacting the o-dialkylbenzene with hydrogen in the presence of a catalyst containing at least one selected from the group consisting of palladium and ruthenium, and a solid acid catalyst containing a lanthanoid metal.

4. A method comprising
subjecting a 3,3',4,4'-tetraalkyl cyclohexylbenzene represented by the general formula (1):

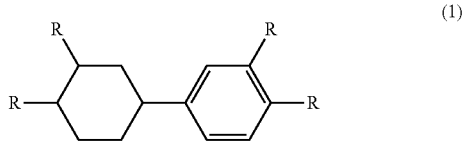

(1)

wherein R represents an alkyl group having 1 to 4 carbon atoms,
to a dehydrogenation reaction, thereby producing a 3,3',4,4'-tetraalkylbiphenyl represented by the general formula (3):

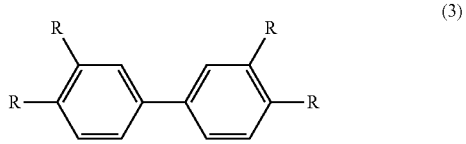

(3)

wherein R is defined as above.

5. A method comprising
performing a hydroalkylation of an o-dialkylbenzene represented by the general formula (2) in accordance with the method according to Item 2 to produce a 3,3',4,4'-tetraalkyl cyclohexylbenzene represented by the general formula (1); and then
subjecting the 3,3',4,4'-tetraalkyl cyclohexylbenzene to a dehydrogenation reaction in accordance with the method according to Item 4 to produce a 3,3',4,4'-tetraalkylbiphenyl represented by the general formula (3).

6. A catalyst for a hydroalkylation reaction, comprising
a catalyst containing at least one selected from the group consisting of palladium and ruthenium; and
a solid acid catalyst containing a lanthanoid metal.

7. The catalyst for a hydroalkylation reaction according to Item 6, wherein the catalyst for a hydroalkylation reaction is to be used in the method according to Item 2.

Advantageous Effects of Invention

According to the present invention, there may be provided a 3,3',4,4'-tetraalkyl cyclohexylbenzene such as 3,3',4,4'-tetramethyl cyclohexylbenzene which may be converted into, for example, a 3,3',4,4'-biphenyltetracarboxylic acid (hereinafter, sometimes referred to as s-BPTA) and a 3,3',4,4'-biphenyltetracarboxylic dianhydride thereof (hereinafter, sometimes referred to as s-BPDA), which are a starting material for a polyimide, via a 3,3',4,4'-tetraalkylbiphenyl (hereinafter, sometimes referred to as s-TABP).

According to the present invention, there may be also provided a method for producing a 3,3',4,4'-tetraalkyl cyclohexylbenzene with high yield and high selectivity from an o-dialkylbenzene efficiently and easily.

DESCRIPTION OF EMBODIMENTS 3,3',4,4'-tetraalkyl cyclohexylbenzene (s-TACHB)

A 3,3',4,4'-tetraalkyl cyclohexylbenzene (s-TACHB) of the present invention is a novel compound represented by the general formula (1).

In the general formula (1), R represents an alkyl group having 1 to 4 carbon atoms. Examples of R include methyl group, ethyl group, n-propyl group, isopropyl group, n-butyl group, and isobutyl group. Among them, methyl group and ethyl group are preferred, and methyl group is more preferred.

The compound may be converted into s-TABP by subjecting the compound to a dehydrogenation reaction in accordance with a known method.

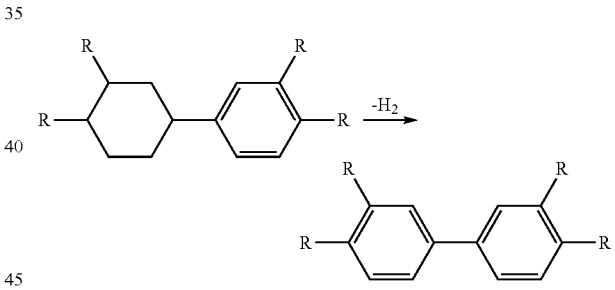

wherein R is defined as above.

One example is as follows. While nitrogen gas is passed through a vertical reactor made of glass, which is charged with 0.9 g of 1 wt % Pd/activated carbon as a catalyst and 1 mm-glass beads thereon, at a rate of 100 ml/min from the upper portion of the reactor, a tubular furnace is heated such that an external temperature reaches 370° C. And then, a reaction solution containing s-TACHB is diluted with heptane to provide a 30-50 wt % reaction solution/n-heptane, and the resultant solution is supplied by a syringe pump to the upper portion of the glass reactor in the tubular furnace at a rate of 0.05 ml/min. The reaction solution which has been passed through the catalyst layer is collected with dry ice-ethanol to obtain s-TABP as a result of a dehydrogenation reaction. The method for the dehydrogenation reaction is not limited to this method.

Furthermore, s-TABP may be converted into a 3,3',4,4'-biphenyltetracarboxylic acid (s-BPTA) and a 3,3',4,4'-biphenyltetracarboxylic dianhydride thereof (s-BPDA) in accordance with a known oxidation method.

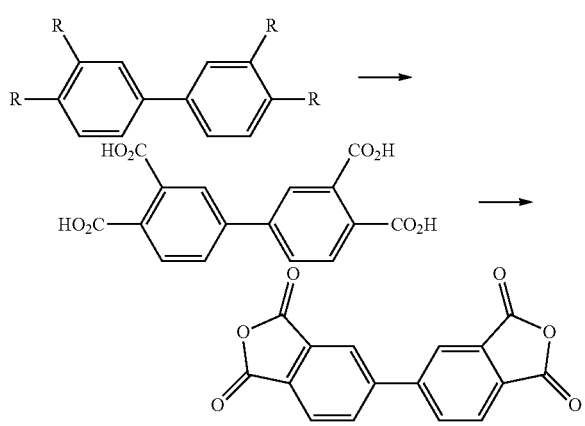

wherein R is defined as above.

One example is as follows. Into an autoclave made of titanium and having an interior volume of 100 mL are placed 2.10 g (10 mmol) of s-TABP, 12.4 mg (0.05 mmol) of cobalt acetate tetrahydrate, 12.2 mg (0.05 mmol) of manganese acetate tetrahydrate, 163 mg (1.0 mmol) of N-hydroxyphthalimide (hereinafter, referred to as NHPI), and 15 ml of acetic acid. And then, a reaction is initiated in an air atmosphere (internal pressure: 3 MPa) at 150° C. The reactor is cooled to room temperature 1 hour after the initiation of the reaction, and the gas is released from the reactor. The same amount of NHPI was added to the resultant reaction solution, and then the reaction was initiated again at 150° C. The series of operations (cooling-pressure release-addition-re-pressurizing/heating with stirring) are repeated again 1 hour after the initiation of the reaction, to perform the reaction for 3 hours in total. After the completion of the reaction, the reactor was cooled to room temperature, and the gas was released from the reactor. The solvent is distilled off from the resultant reaction solution. Subsequently, ethyl acetate and water are added to the resultant solution, and then the layers are separated. And then, the ethyl acetate layer is washed with water to remove a metal compound and s-BPTA is obtained. The oxidation method is not limited to this method.

Production of a 3,3',4,4'-tetraalkyl cyclohexylbenzene (s-TACHB) (Hereinafter, Sometimes Referred to as Hydroalkylation Reaction)

An s-TACHB of the present invention may be obtained by a hydroalkylation of o-dialkylbenzene, and many various regioisomers are formed according to the reacting sites of the o-dialkylbenzene as a starting material. More specifically, 4 types of o-dialkylcyclohexenes are formed from an o-dialkylbenzene by partial reduction with hydrogen first. The reaction in the case where R is methyl group (Me), for example, is represented by the following formula.

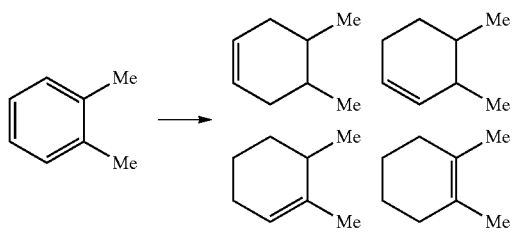

Subsequently, an o-dialkylbenzene reacts with these 4 types of isomers. Accordingly, many various isomers are formed. The reaction in the case where R is methyl group (Me), for example, is represented by the following formula.

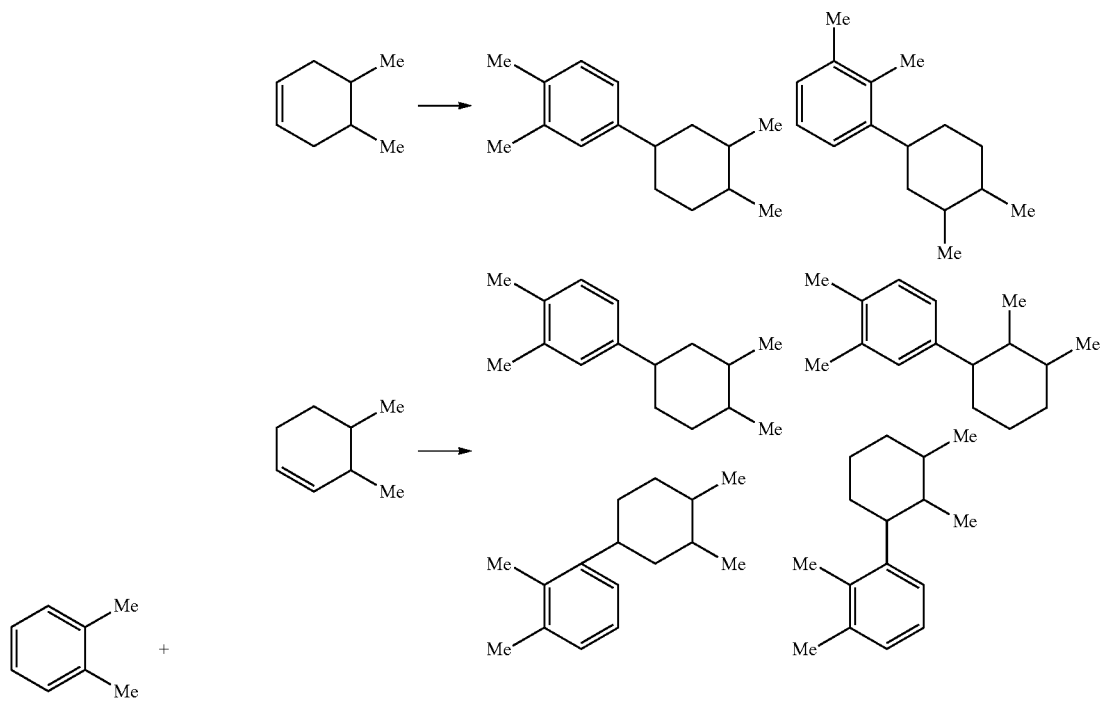

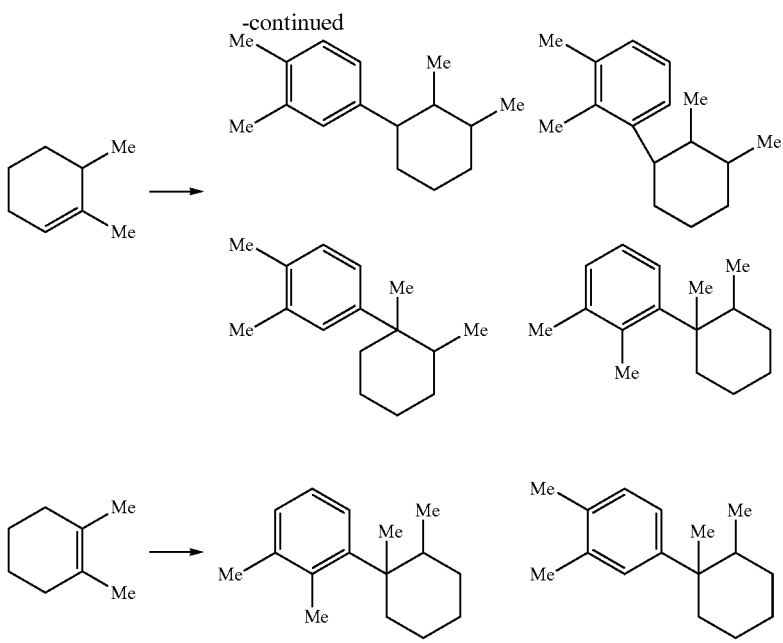

As shown in the following formulas, the isomers as described above may be broadly classified into 4 types:

s-TACHB which may be converted into s-TABP by a dehydrogenation reaction;

a-TACHB (2 types) which may be converted into a-TABP by a dehydrogenation reaction;

i-TACHB which may be converted into i-TABP by a dehydrogenation reaction; and q-TABP which may not be converted into a biphenyl.

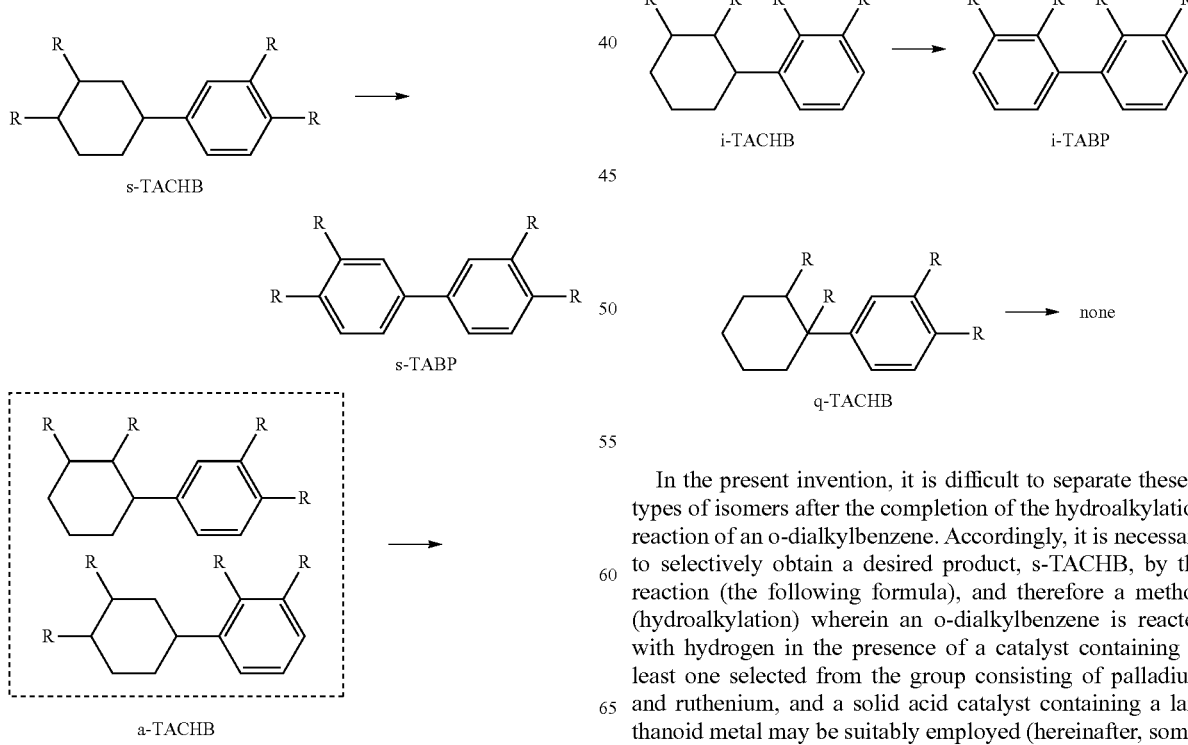

In the present invention, it is difficult to separate these 4 types of isomers after the completion of the hydroalkylation reaction of an o-dialkylbenzene. Accordingly, it is necessary to selectively obtain a desired product, s-TACHB, by the reaction (the following formula), and therefore a method (hydroalkylation) wherein an o-dialkylbenzene is reacted with hydrogen in the presence of a catalyst containing at least one selected from the group consisting of palladium and ruthenium, and a solid acid catalyst containing a lanthanoid metal may be suitably employed (hereinafter, sometimes referred to as the reaction of the present invention).

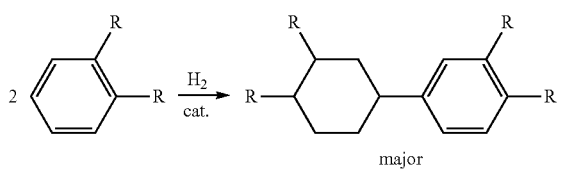

wherein R is defined as above.

In the s-TACHB (desired product) obtained directly by the reaction of the present invention, two alkyl groups present on the cyclohexyl group form a plurality of steric configurations, as shown in the following formula. However, all of them may be converted into s-TABP by a dehydrogenation reaction, and therefore may be regarded as desired products.

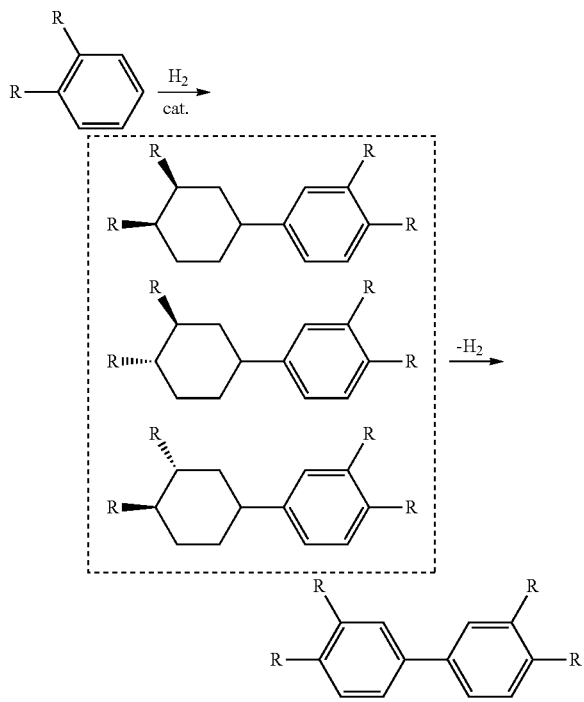

wherein R is defined as above.

o-Dialkylbenzene

The o-dialkylbenzene to be used in the reaction of the present invention is a compound represented by the general formula (2), and in the general formula (2), R is defined as above and represents an alkyl group having 1 to 4 carbon atoms.

(Catalyst Containing at Least One Selected from the Group Consisting of Palladium and Ruthenium)

The catalyst containing at least one selected from the group consisting of palladium and ruthenium to be used in the present invention may be a palladium catalyst containing palladium, a ruthenium catalyst containing ruthenium, or a mixture thereof (hereinafter, sometimes referred to as palladium/ruthenium catalyst). Herein, the palladium catalyst and the ruthenium catalyst may be used alone, or in a form of the catalyst supported on an inactive support. In the cases of mixture catalysts, either the palladium catalyst or the ruthenium catalyst may be supported on a support, or both the catalysts may be supported on a support.

Examples of the palladium catalyst include metal palladium, palladium black; inorganic palladium salts such as palladium chloride, palladium bromide, palladium iodide, palladium sulfate, and palladium nitrate; organic acid salts such as palladium acetate, and palladium oxalate; and palladium complex compounds in which acetylacetonato, carbon monoxide, a nitrile, an amine, a phosphine, or an olefin coordinates to palladium, for example, palladium complex compounds such as tetra(ammine)palladium dichloride, dichlorodiacetonitrile palladium, and dichlorobis(triphenylphosphine) palladium. Among them, palladium acetate, palladium chloride, or tetra(ammine)palladium dichloride may be preferably used. These palladium catalysts may be used alone, or as a mixture of two or more types. The palladium complex compound may be prepared in advance and then used, or alternatively, compounds forming the palladium complex compound may be separately added into a reaction system to prepare the palladium complex compound in the reaction system.

Examples of the ruthenium catalyst include metal ruthenium, ruthenium black; inorganic ruthenium salts such as ruthenium chloride, ruthenium bromide, ruthenium iodide, ruthenium sulfate, and ruthenium nitrate; organic acid salts such as ruthenium acetate; and ruthenium complex compounds in which acetylacetonato, carbon monoxide, a nitrile, an amine, a phosphine, or an olefin coordinates to ruthenium, for example, ruthenium complex compounds such as hexa(ammine)ruthenium trichloride. Among them, ruthenium chloride, hexa(ammine)ruthenium trichloride, or tris(acetylacetonato)ruthenium may be preferably used. These ruthenium catalysts may be used alone, or as a mixture of two or more types. The ruthenium complex compound may be prepared in advance and then used, or alternatively, compounds forming the ruthenium complex compound may be separately added into a reaction system to prepare the ruthenium complex compound in the reaction system.

Examples of the support on which the palladium catalyst and/or the ruthenium catalyst are supported include carbon, silica, alumina, silica-alumina, zirconia, titania, ceria, zeolite, mesoporous silica, hydroxyapatite, and clays such as hydrotalcite.

As a method for preparing the palladium/ruthenium catalyst supported on a support, a commonly-used method such as an evaporation-to-dryness method, an impregnation method, a pore-filling method, and an ion exchange method may be used. A pore-filling method or an ion exchange method may be preferred in view of improvement in dispersibility of the metal ion supported on the inorganic structure, but the preparation method is not limited to them. The catalyst may be calcined in an inert gas atmosphere after the palladium/ruthenium catalyst is supported on the support.

Furthermore, prior to the reaction, the palladium/ruthenium catalyst (a palladium catalyst containing palladium, a ruthenium catalyst containing ruthenium, or a mixture thereof) may be subjected to a reduction treatment using a reducing agent such as hydrogen The amount of the palladium/ruthenium catalyst to be used may be preferably $10^{-7}$ to $10^{-2}$ mole, more preferably $10^{-6}$ to $10^{-3}$ mole, per mole of the o-dialkylbenzene in terms of metal molar ratio. When the amount falls within the range, s-TACHB may be selectively produced while suppressing incomplete hydrogen reduction and excessive hydrogen reduction of the o-dialkylbenzene.

(Solid Acid Catalyst Containing a Lanthanoid Metal)

The solid acid catalyst containing a lanthanoid metal to be used in the reaction of the present invention may be, for example, a lanthanoid metal oxide, or a catalyst containing a lanthanoid metal supported on a support such as a proton type zeolite. Herein, the lanthanoid metal is the general term for chemical elements of atomic number 57 to 71, and may be preferably lanthanum, cerium, praseodymium, neodymium, samarium, or ytterbium.

The lanthanoid metal oxide may be an oxide of one or more lanthanoid metals, a composite oxide of one or more lanthanoid metals and one or more other metals, or a physical mixture thereof, as long as the lanthanoid metal oxide functions as a solid acid catalyst.

The support for the catalyst in which a lanthanoid metal is supported on the support may be preferably an inorganic structure containing silicon and aluminum as the main components, for example. Examples of the inorganic structure containing silicon and aluminum as the main components include silica-alumina, zeolite, mesoporous silica, hydroxyapatite, and clays such as hydrotalcite. Among them, a zeolite may be particularly suitably used.

Examples of the zeolite include, but not limited to, Y type, A type, ferrierite type, ZSM-5 (MFI type), ZSM-12 (MTW type), mordenite type, beta type, X type, and T type, all of which may be used. In addition, zeolites in which cations are exchanged ($H^+$, $NH_4^+$, metal ion, etc.), zeolites in which Si/Al ratios in zeolitic frameworks are changed, zeolites in which other metals such as Ti, Sn, and Zr substitute for Si and/or Al in zeolitic frameworks, and the like may be also used. Commercially available products may be used as the zeolite.

The Si/Al ratio of the zeolite may be preferably, but not limited to, 0.01 to 100, further preferably 1 to 80, more preferably 2 to 60.

A method for supporting a lanthanoid metal on a support may be, but not limited to, an evaporation-to-dryness method, an impregnation method, a pore-filling method, or an ion exchange method, for example. In view of improvement in dispersibility of the lanthanoid metal supported on the support (solid acid), a pore-filling method or an ion exchange method may be preferably employed.

The amount of the lanthanoid metal supported may be preferably 1 to 30 wt %, more preferably 3 to 20 wt %, based on the total weight of the catalyst. When the amount falls within the range, s-TACHB may be selectively produced while accelerating the reaction of an o-dialkylcyclohexene, which is produced by hydrogen reduction of an o-dialkylbenzene, and an o-dialkylbenzene.

It is desirable that the solid acid catalyst containing a lanthanoid metal be used in the reaction after removal of water adsorbed thereon, in view of the attainment of catalytic activity. As the method for removing water, a method wherein the catalyst is calcined in an inert gas atmosphere such as nitrogen atmosphere and argon atmosphere preferably at 400 to 600° C. for 1 to 12 hours, for example, may be suitably employed. In the case of a catalyst containing a lanthanoid metal supported on a support, it is desirable that the catalyst be dried, and then calcined after the lanthanoid metal is supported on the support. When the water is removed, a sufficient catalytic activity may be attained, and decreases in activity and selectivity for the desired product may be prevented.

The amount of the solid acid catalyst containing a lanthanoid metal to be used may be preferably 0.01 to 200 wt %, more preferably 0.1 to 100 wt %, based on the weight of the o-dialkylbenzene. When the amount of the solid acid catalyst containing a lanthanoid metal as a catalyst for the alkylation reaction is too small, a sufficient reaction rate may not be attained. When the amount is too large, that is uneconomical. When the amount falls within the range, s-TACHB may be selectively produced while accelerating the reaction of an o-dialkylcyclohexene, which is produced by hydrogen reduction of an o-dialkylbenzene, and an o-dialkylbenzene.

(Reaction Conditions)

The reaction of the present invention may be performed, for example, by a method comprising mixing an o-dialkylbenzene, a catalyst containing at least one selected from the group consisting of palladium and ruthenium, and a solid acid catalyst containing a lanthanoid metal, and then stirring the resultant mixture in a hydrogen gas atmosphere to perform the reaction. In that case, the reaction temperature is preferably 80 to 500° C., more preferably 100 to 400° C., and the reaction pressure is preferably 0.01 to 8.0 MPa, more preferably 0.05 to 5.0 MPa. The reaction mode may be any mode, including batch or flow mode, vapor phase or liquid phase, and fixed bed or fluidized bed. The reaction may be preferably performed in a flow mode using a fixed bed.

The amount of hydrogen to be used in the reaction of the present invention may be preferably 2 to 100000 moles, more preferably 3 to 10000 moles, particularly preferably 6 to 1000 moles, per mole of the o-dialkylbenzene. When the amount falls within the range, s-TACHB may be selectively produced while suppressing incomplete hydrogen reduction and excessive hydrogen reduction of the o-dialkylbenzene.

After the completion of the reaction, s-TACHB obtained by the reaction of the present invention may be isolated and purified by a common method such as filtration, extraction, distillation, sublimation, recrystallization, and column chromatography.

As described above, the obtained s-TACHB may be converted into s-TABP by a dehydrogenation reaction, and s-TABP may be converted into s-BPTA by an oxidation of alkyl groups of the s-TABP, and s-BPTA may be further converted into s-BPDA by a dehydration reaction.

Analysis of 3,3',4,4'-tetraalkyl cyclohexylbenzene (s-TACHB)

As described above, 4 types of isomers, into which s-TACHB is broadly classified, may be produced by the reaction of the present invention, and it is difficult to analyze the isomers individually and it is also difficult to separate the isomers. For that reason, the mixture of these 4 types of isomers may be converted into the corresponding biphenyl compounds by a dehydrogenation reaction to determine the amount of each isomer produced. More specifically, the desired product of the present invention, s-TACHB, may be converted into s-TABP such as s-TMBP to determine the amount thereof. This conversion is sometimes referred to as a dehydrogenation reaction. The dehydrogenation reaction to convert s-TACHB into s-TABP may be performed as described above.

(Catalyst of the Present Invention)

The catalyst of the present invention comprises the catalyst containing at least one selected from the group consisting of palladium and ruthenium, and the solid acid catalyst containing a lanthanoid metal. The catalyst may be also effective as a catalyst for hydroalkylation reactions other than the reaction of the present invention, that is, a hydroalkylation reaction of an o-dialkylbenzene.

EXAMPLES

The present invention will be specifically described below with reference to the Examples; however, the scope of the present invention is not limited to these Examples. The analysis of reaction products was conducted with gas chromatography (FID detector, internal reference method), and the amounts of metal atoms in the resultant solid substances (catalysts) were analyzed by ICP (Inductively Coupled Plasma).

The abbreviations are as follows.
o-Xy: o-xylene (1,2-dimethylbenzene)
TMCHB: tetramethyl cyclohexylbenzene (including all isomers)
s-TMCHB: 3,3',4,4'-tetramethyl cyclohexylbenzene
a-TMCHB: 2,3,3',4'-tetramethyl cyclohexylbenzene and 2',3,3',4-tetramethyl cyclohexylbenzene
i-TMCHB: 2,2'3,3'-tetramethyl cyclohexylbenzene
q-TMCHB: 1,2,3',4'-tetramethyl cyclohexylbenzene
DMCy: 1,2-dimethylcyclohexane
TMBP: tetramethylbiphenyl
s-TMBP: 3,3',4,4'-tetramethylbiphenyl Preparation for Solid Acid Catalyst Containing a Lanthanoid Metal Example 1A Synthesis of Lanthanium-Supported Zeolite
(Hereinafter, Also Referred to as La/HY Catalyst)

A solution prepared by dissolving 3 g of lanthanum nitrate hexahydrate in 100 ml of deionized water was added drop by drop at room temperature to a suspension prepared by mixing 6 g of H-type Y zeolite (HSZ-320HOA; manufactured by Tosoh Corporation) (Si/Al ratio=2.8) and 200 ml of deionized water, and the resultant mixture was stirred at 110° C. for 4 hours. After the completion of stirring, a solid substance was separated using a centrifuge, washed with 45 ml of deionized water 5 times, and then dried at 110° C. overnight. After the completion of drying, the resultant substance was calcined in a nitrogen atmosphere at 550° C. for 3 hours to obtain a solid lewis acid catalyst containing a lanthanoid metal (La/HY). The obtained solid substance (La/HY) was analyzed by ICP (Inductively Coupled Plasma). The amount of lanthanum atom in the solid substance was 5.6 wt %.

Example 2A

Preparation for Samarium-Supported Zeolite
(Hereinafter, Also Referred to as Sm/HY Catalyst)

A solid lewis acid catalyst containing a lanthanoid metal (Sm/HY) was obtained in the same manner as in Example 1A except that samarium nitrate hexahydrate was used instead of lanthanum nitrate hexahydrate in Example 1A. The amount of samarium atom in the obtained solid substance (Sm/HY) was 5.6 wt %.

Example 3A

Preparation for Cerium-Supported Zeolite
(Hereinafter, Also Referred to as Ce/HY Catalyst)

A solid lewis acid catalyst containing a lanthanoid metal (Ce/HY) was obtained in the same manner as in Example 1A except that cerium nitrate hexahydrate was used instead of lanthanum nitrate hexahydrate in Example 1A. The amount of cerium atom in the obtained solid substance (Ce/HY) was 4.6 wt %.

Example 4A

Preparation for Yttrium-Supported Zeolite
(Hereinafter, Also Referred to as Y/HY Catalyst)

A solid lewis acid catalyst containing a lanthanoid metal (Y/HY) was obtained in the same manner as in Example 1A except that yttrium nitrate hexahydrate was used instead of lanthanum nitrate hexahydrate in Example 1A. The amount of yttrium atom in the obtained solid substance (Y/HY) was 2.9 wt %.

Preparation for Palladium Catalyst, Ruthenium Catalyst, and Other Catalysts

Example 5A

Synthesis of Palladium-Supported γ-Alumina
(Hereinafter, Also Referred to as Pd/γ-$Al_2O_3$ Catalyst)

A solution was prepared by dissolving 0.045 g of palladium acetate in 5 ml of acetone, and then 2 g of γ-$Al_2O_3$ (manufactured by STREM CHEMICALS Inc.) was added to this solution, and impregnation was performed at room temperature for 1 hour. Subsequently, the liquid portion of the obtained suspension was evaporated to dry, and then dried. The resultant substance was subjected to a reduction treatment in a hydrogen stream at 200° C. for 2 hours. The amount of palladium atom in the obtained solid substance (Pd/γ-$Al_2O_3$) was 1.0 wt %.

Example 6A

Preparation for Ruthenium-Supported γ-Alumina
(Hereinafter, Also Referred to as Ru/γ-$Al_2O_3$ Catalyst)

A ruthenium-containing Ru/γ-$Al_2O_3$ was obtained in the same manner as in Example 5A except that ruthenium acetylacetonato was used instead of palladium acetate in Example 5A. The resultant substance was subjected to a reduction treatment in a hydrogen stream at 200° C. for 2 hours. The amount of ruthenium atom in the obtained solid substance (Ru/γ-$Al_2O_3$) was 1.0 wt %.

Reference Example 1

Preparation for Platinum-Supported Carbon
(Hereinafter, Also Referred to as Pt/C Catalyst)

A platinum-containing Pt/C was obtained in the same manner as in Example 5A except that chloroplatinic acid was used instead of palladium acetate and an activated carbon (manufactured by Tokyo Chemical Industry Co., Ltd.) was used as a support in Example 5A. The resultant substance was subjected to a reduction treatment in a hydrogen stream at 200° C. for 2 hours. The amount of platinum atom in the obtained solid substance (Pt/C) was 3.4 wt %.

Reference Example 2

Preparation for Rhodium-Supported Carbon
(Hereinafter, Also Referred to as Rh/C Catalyst)

A rhodium-containing Rh/C was obtained in the same manner as in Reference Example 1 except that rhodium chloride was used instead of chloroplatinic acid in Reference Example 1. The amount of rhodium atom in the obtained solid substance (Rh/C) was 2.5 wt %.

Reference Example 3

Preparation for Iridium-Supported Carbon
(Hereinafter, Also Referred to as Ir/C Catalyst)

A iridium-containing Ir/C was obtained in the same manner as in Reference Example 1 except that iridium chloride acid was used instead of chloroplatinic acid in Reference Example 1. The amount of iridium atom in the obtained solid substance (Ir/C) was 1.0 wt %.

Example 1B

Hydroalkylation Reaction; Synthesis of 3,3',4,4'-tetramethyl cyclohexylbenzene (s-TMCHB)

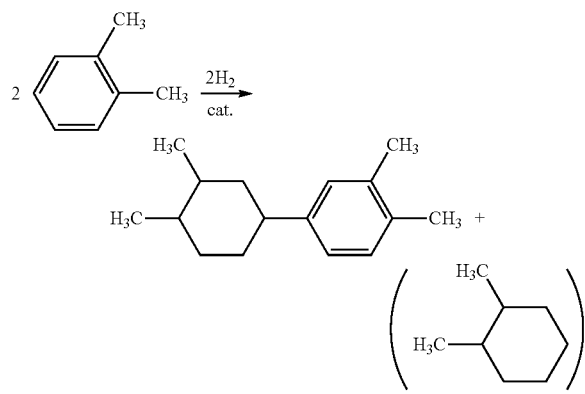

0.15 g of La/HY (La in the catalyst: 0.05 mmol), 0.03 g of Pd/γ-Al₂O₃ (Pd in the catalyst: 0.003 mmol), and 1 g (9.42 mmol) of o-xylene were added into an inner glass tube having an interior volume of 50 ml in an autoclave made of SUS and having the inner glass tube. After the reaction system was purged with hydrogen gas, hydrogen gas was supplied to the reaction system until the pressure was 1.6 MPa. Subsequently, the autoclave was immersed in an oil bath set at 150° C. previously, and the reaction was performed for 4 hours.

After the completion of the reaction, the autoclave was cooled with water, and the gas was released from the reactor. The resultant reaction solution was analyzed. The conversion of o-xylene (o-Xy) was 36.9%, and tetramethyl cyclohexylbenzene (TMCHB) was produced with a yield of 27M % and a selectivity of 74.8% (based on converted o-Xy). In addition, a by-product, dimethylcyclohexane (DMCy) was produced with a yield of 3.4% and a selectivity of 9.2% (based on converted o-Xy).

Subsequently, TMCHB was converted into TMBP by subjecting TMCHB to a dehydrogenation reaction, to determine the amount of s-TMCHB in TMCHB.

Dehydrogenation Reaction

Synthesis of 3,3',4,4'-tetramethylbiphenyl (s-TMBP)

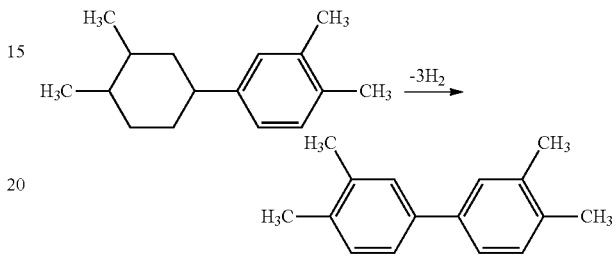

A vertical reactor made of SUS was charged with 1 ml of 1 wt % Pd/C catalyst and 1 mm-glass beads thereon. Subsequently, while nitrogen gas was passed through the reactor at a rate of 100 ml/min, the reactor was heated in a tubular furnace such that the external temperature reached 370° C., and maintained at the temperature for 1 hour. Subsequently, the reaction solution obtained in Example 1B was diluted to provide a 30 wt % TMCHB/n-heptane, and then the resultant solution was supplied by a supply pump to the upper portion of the glass beads layer at a rate of 0.05 ml/min. The reaction solution which had been passed through the catalyst layer was collected with dry ice-ethanol. The resultant reaction solution was analyzed. 3,3',4,4'-tetramethylbiphenyl (s-TMBP) was produced with a selectivity of 49.7% (based on converted TMCHB) (i.e., the selectivity of s-TMCHB in the hydroalkylation reaction was 37.1% (based on converted o-Xy)).

Examples 2B to 10B and Comparative Examples 1 to 5

Synthesis of 3,3',4,4'-tetramethyl cyclohexylbenzene (s-TMCHB) and 3,3',4,4'-tetramethylbiphenyl (s-TMBP)

The reactions were performed in the same manner as in Example 1B except that the type of catalyst, reaction temperature, and hydrogen pressure in Example 1B were changed to those shown in Table 1. The results are shown in Table 1.

TABLE 1

| | Catalyst | Solid acid catalyst containing lanthanoid metal | o-Xy conversion (%) | TMCHB yield (%) (selectivity (%)) | DMCy yield (%) (selectivity (%)) | s-TMBP selectivity (%) |
|---|---|---|---|---|---|---|
| Example 1B | Pd/ γ-Al₂O₃ | La/HY | 36.9 | 27.6 (74.8) | 3.4 (9.2) | 49.7 |
| Comparative Example 1 | None | La/HY | 5.9 | 0 | 0 | |
| Comparative Example 2 | Pd/ γ-Al₂O₃ | None | 18.2 | 0 | 11.0 (61.0) | |

TABLE 1-continued

| | Catalyst | Solid acid catalyst containing lanthanoid metal | o-Xy conversion (%) | TMCHB yield (%) (selectivity (%)) | DMCy yield (%) (selectivity (%)) | s-TMBP selectivity (%) |
|---|---|---|---|---|---|---|
| Example 2B | Pd/γ-Al$_2$O$_3$ | Sm/HY | 38.5 | 27.1 (70.4) | 3.3 (8.6) | 44.6 |
| Example 3B | Pd/γ-Al$_2$O$_3$ | Ce/HY | 21.7 | 14.6 (67.3) | 0.8 (3.7) | |
| Example 4B | Pd/γ-Al$_2$O$_3$ | Y/HY | 19.5 | 8.5 (43.6) | 0.6 (3.1) | |
| Example 5B | Pd/Al-HMS | La/HY | 41.4 | 30.5 (73.7) | 5.4 (13.0) | |
| Example 6B | Ru/γ-Al$_2$O$_3$ | La/HY | 50.2 | 37.1 (73.9) | 11.1 (22.1) | 46.0 |
| Comparative Example 3 | Pt/C | La/HY | 79.0 | 21.4 (27.1) | 39.8 (50.4) | 9.0 |
| Comparative Example 4 | Rh/C | La/HY | 14.9 | 3.1 (20.8) | 0.6 (4.0) | 1.1 |
| Comparative Example 5 | Ir/C | La/HY | 89.8 | 18.2 (20.3) | 49.8 (55.5) | 7.5 |
| Example 7B | Pd/γ-Al$_2$O$_3$ | La/HY | 34.9 | 28.7 (82.2) | 2.8 (8.0) | |
| Example 8B | Pd/γ-Al$_2$O$_3$ | La/HY | 51.4 | 29.8 (58.0) | 4.4 (8.6) | |
| Example 9B | Pd/γ-Al$_2$O$_3$ | La/HY | 23.8 | 6.6 (27.7) | 0.9 (3.4) | |
| Example 10B | Pd/γ-Al$_2$O$_3$ | La/HY | 59.9 | 26.6 (44.4) | 9.9 (16.5) | |

Reaction temperature; 150° C. (Example 9B: 120° C., Example 10B: 170° C.)
Hydrogen pressure; 1.6 MPa (Example 7B: 1.0 MPa, Example 8B: 3.0 MPa)
TMCHB selectivity and DMCy selectivity are calculated based on converted o-Xy, and s-TMBP selectivity is calculated based on converted TMCHB.

As can be seen from these results, a desired product, 3,3',4,4'-tetraalkyl cyclohexylbenzene may be obtained with high yield and high selectivity by the hydroalkylation reaction of the present invention, more specifically, by reacting o-xylene with hydrogen in the presence of a palladium catalyst or a ruthenium catalyst, and a solid lewis acid catalyst containing a lanthanoid metal.

INDUSTRIAL APPLICABILITY

According to the present invention, there may be provided a novel 3,3',4,4'-tetraalkyl cyclohexylbenzene. The compound is a useful compound which may be easily converted into, for example, a 3,3',4,4'-biphenyltetracarboxylic acid and a 3,3',4,4'-biphenyltetracarboxylic dianhydride thereof, which are a starting material for a polyimide, via a 3,3',4,4'-tetraalkylbiphenyl.

The invention claimed is:

1. A method comprising:
reacting an o-dialkylbenzene represented by the general formula (2):

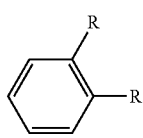

(2)

wherein R represents an alkyl group having 1 to 4 carbon atoms, with hydrogen in the presence of a catalyst containing at least one selected from the group consisting of palladium and ruthenium, and a solid acid catalyst containing a lanthanoid metal to perform a hydroalkylation of the o-dialkylbenzene, thereby producing a 3,3',4,4'-tetraalkyl cyclohexylbenzene represented by the general formula (1):

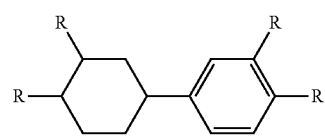

(1)

wherein R is defined as above.

* * * * *